US010864152B2

(12) United States Patent
Stewart

(10) Patent No.: US 10,864,152 B2
(45) Date of Patent: Dec. 15, 2020

(54) TRPV3 AGONISTS FOR THE TREATMENT OF SKIN CONDITIONS

(71) Applicant: John M. Stewart, Sackville (CA)

(72) Inventor: John M. Stewart, Sackville (CA)

(73) Assignee: Soricimed Biopharma Inc., New Brunswick (CA)

( * ) Notice: Subject to any disclaimer, the term of this patent is extended or adjusted under 35 U.S.C. 154(b) by 0 days.

(21) Appl. No.: 15/704,581

(22) Filed: Sep. 14, 2017

(65) Prior Publication Data

US 2018/0085296 A1   Mar. 29, 2018

Related U.S. Application Data

(63) Continuation of application No. 14/428,209, filed as application No. PCT/CA2013/000788 on Sep. 16, 2013, now abandoned.

(60) Provisional application No. 61/701,128, filed on Sep. 14, 2012.

(51) Int. Cl.

| | |
|---|---|
| *A61K 8/64* | (2006.01) |
| *A61Q 19/08* | (2006.01) |
| *A61K 38/08* | (2019.01) |
| *C07K 7/06* | (2006.01) |
| *C07K 14/47* | (2006.01) |
| *A61K 38/17* | (2006.01) |
| *A61K 38/10* | (2006.01) |
| *A61Q 19/00* | (2006.01) |

(52) U.S. Cl.
CPC ............... *A61K 8/64* (2013.01); *A61K 38/08* (2013.01); *A61K 38/10* (2013.01); *A61K 38/17* (2013.01); *A61K 38/1709* (2013.01); *A61Q 19/00* (2013.01); *A61Q 19/08* (2013.01); *C07K 7/06* (2013.01); *C07K 14/47* (2013.01); *C07K 14/4747* (2013.01)

(58) Field of Classification Search
None
See application file for complete search history.

(56) References Cited

U.S. PATENT DOCUMENTS

| | | |
|---|---|---|
| 7,119,168 B2 | 10/2006 | Stewart et al. |
| 7,273,850 B2 | 9/2007 | Stewart et al. |
| 7,485,622 B2 | 2/2009 | Stewart et al. |
| 7,745,588 B2 | 6/2010 | Stewart et al. |
| 8,003,754 B2 | 8/2011 | Stewart et al. |
| 8,211,857 B2 | 7/2012 | Stewart |
| 8,338,136 B2 | 12/2012 | Stewart et al. |
| 8,618,058 B2 | 12/2013 | Stewart |
| 8,673,858 B2 | 3/2014 | Stewart et al. |
| 8,962,817 B2 | 2/2015 | Stewart et al. |
| 9,181,219 B2 * | 11/2015 | Moran ............... C07D 401/12 |
| 2010/0137260 A1 | 6/2010 | Hwang et al. |
| 2010/0329983 A1 | 12/2010 | Stewart |
| 2011/0071089 A1 * | 3/2011 | Stewart ............... C07K 14/4703 514/18.9 |
| 2014/0187493 A1 | 7/2014 | Stewart |

FOREIGN PATENT DOCUMENTS

| | | |
|---|---|---|
| WO | WO 2004/046178 | 6/2004 |
| WO | WO 2009/114943 | 9/2009 |
| WO | WO 2010/148501 | 12/2010 |

OTHER PUBLICATIONS

Veness et al., Head and Neck, 29(7):621-631, 2007.*
Borbiro, I., et al., "Activation of transient receptor potential vanilloid-3 inhibits human hair growth." Journal of Investigative Dermatology, Aug. 2011, vol. 131, No. 8, pp. 1605-1614.
Cao, X., et al., "Intracellular Proton-mediated Activation of TRPV3 Channels Accounts for the Exfoliation Effect of αHydroxyl Acids on Keratinocytes." The Journal of Biological Chemistry, Jul. 27, 2012, vol. 287, No. 31, pp. 25905-25916.
Lee, J., et al., "Mechanisms of carvacrol-induced expression of type I collagen gene." Journal of Dermatological Science, 2008, vol. 52(3), pp. 160-169.
Miyamoto, T., et al., "TRPV3 regulates nitric oxide synthase-independent nitric oxide synthesis in the skin." Nat Commun., Jun. 28, 2011, vol. 2, 369.
Moussaieff, A., et al., "Incensole acetate, an incense component, elicits psychoactivity by activating TRPV3 channels in the brain." The FASEB Journal, Aug. 2008, vol. 22(8), pp. 3024-3034.
Written Opinion (completed Dec. 12, 2013) and International Search Report (completed Dec. 5, 2013) for corresponding PCT Application No. PCT/CA2013/000788.
Vriens, J., et al., "Pharmacology of vanilloid transient receptor potential cation channels." Molecular Pharmacology, Jun. 2009, vol. 75, No. 6, pp. 1262-1279. doi: 10.1124/mol.109.055624. Epub Mar. 18, 2009.
Lai-Cheong, J.E., et al., "Recurrent heterozygous missense mutation, p.Gly573Ser, in the TRPV3 gene in an Indian boy with sporadic Olmsted syndrome." British Journal of Dermatology, Aug. 2012, vol. 167, Issue 2, pp. 440-442.
Moran, M.M., et al., "Transient receptor potential channels as therapeutic targets." Nature Reviews, Drug Discovery, Aug. 1, 2011, vol. 10, No. 8, pp. 601-620.

(Continued)

*Primary Examiner* — Marianne P Allen

(74) *Attorney, Agent, or Firm* — Bereskin & Parr LLP/S.E.N.C.R.L., s.r.l.; Laurence MacPhie

(57) ABSTRACT

Described are methods and uses of TRPV3 agonists for the treatment of conditions associated with TRPV3 pathophysiology such as acne, psoriasis, dermatitis, would healing, the inhibition of hair growth, anxiety or depression. Peptides comprising all or part of the C-terminal portion of soricidin are shown to activate TRPV3 cation channel activity and/or promote wound healing in keratinocytes.

6 Claims, 10 Drawing Sheets

Specification includes a Sequence Listing.

(56) References Cited

OTHER PUBLICATIONS

Vay, L, et al., "The thermo-TRP ion channel family: properties and therapeutic implications." British Journal of Pharmacology, Feb. 2012, vol. 165, No. 4, pp. 787-801.
Yamamoto-Kasai, E., et al., "TRPV3 as a Therapeutic Target for Itch." Journal of Investigative Dermatology, Aug. 1, 2012, vol. 132, No. 8, pp. 2109-2112.
Imura, K., et al., "Influence of TRPV3 mutation on hair growth cycle in mice." Biochemical and Biophysical Research Communications, Oct. 6, 2007, vol. 363, No. 3, pp. 479-483.
Supplementary European Search Report for corresponding European Patent Application No. 13837615.7 completed Apr. 28, 2016.
Peier, A.M., et al., "A Heat-Sensitive TRP Channel Expressed in Keratinocytes." Science, Jun. 14, 2002, vol. 296, pp. 2046-2049.
Lehen'Kyi, V., et al., "TRPV6 Is a Ca2+ Entry Channel Essential for Ca2+ -induced Differentiation of Human Keratinocytes." The Journal of Biological Chemistry, Aug. 3, 2007, vol. 282, No. 31, pp. 22582-22591.
Joshi, N.K., et al., "The TRPV3 Receptor as a Pain Target: A Therapeutic Promise or Just Some More New Biology." The Open Drug Discovery Journal, 2010, vol. 2, pp. 89-97.

\* cited by examiner

TRPV3 AGONISTS FOR THE TREATMENT OF SKIN CONDITIONS

RELATED APPLICATIONS

This application is a continuation of U.S. application Ser. No. 14/428,209 filed Mar. 13, 2015 (now abandoned), which is a national phase entry of PCT/CA2013/000788 filed Sep. 16, 2013 (which designates the U.S.), which claims priority to U.S. Provisional Patent Application No. 61/701,128 filed on Sep. 14, 2012, the contents of which are hereby incorporated by reference in their entirety.

INCORPORATION OF SEQUENCE LISTING

A computer readable form of the Sequence Listing "15309-P39153US02_SequenceListing.txt" (4,096 bytes), submitted via EFS-WEB and created on Sep. 14, 2017, is herein incorporated by reference.

FIELD

The present invention relates to Transient Receptor Potential Vanilloid 3 (TRPV3) agonists and more specifically to methods and uses of TRPV3 agonists for the treatment of skin conditions.

INTRODUCTION

Soricidin (NCBI accession no. P0C2C6) is a fifty-four amino acid paralytic peptide isolated from the submaxilary saliva gland of the Northern Short-tailed Shrew (*Blarina brevicauda*). Previous patents have described isolation of the soricidin peptide and provided data showing that the 54-mer peptide caused paralysis and inhibited calcium uptake in two ovarian cancer cell lines (see U.S. Pat. Nos. 7,119,168 and 7,273,850, incorporated by reference herein in their entirety).

Transient Receptor Potential (TRP) channels are calcium ion channels that are found across the invertebrates and vertebrates. The Transient Receptor Potential Vanilloid (TRPV) members of the TRP super-family were named after it was discovered that they activate in the presence of vanilloids (capsaicin from hot peppers for example). The first four of these receptors (TRPV1, TRPV2, TRPV3 and TRPV4) all responded to capsaicin and were also responsible for detecting changes in temperature and other environmental signals. The remaining two of the TRPV sub-family, TRPV5 and TRPV6, were found predominantly in epithelial type or derived tissues and were responsible for influx of calcium ion into the cell.

Peptides corresponding to certain C-terminal sequences of soricidin have been shown to inhibit Transient Receptor Potential Vanilloid channel 6 (TRPV6) without paralytic activity and to be useful for the treatment of cancer, including metastatic cancer (see US Patent application no. 20110071089, incorporated by reference herein in its entirety). The peptides maintain TRPV6 calcium channel binding activity without the sodium-channel binding paralytic activity of the full-length soricidin peptide. While C-terminal soricidin peptides are known to inhibit TRPV6, little is known about their effect on other calcium channels or members of the TRPV family.

TRPV3 is a non-selective cation channel that has been implicated in a variety of physiological processes including temperature sensation and vasoregulation. TRPV3 is expressed predominantly in the brain and in keratinocytes. Activation of TRPV3 has been shown to inhibit human hair growth in vitro and a constitutively active gain-of-function trpv3 mutation in mice resulted in a hairless phenotype (Borbio et al., 2011, Imura et al. 2007). TRPV3 has also been shown to regulate nitric oxide synthesis in the skin (Miyamoto et al. 2012) and activation of TRPV3 with intracellular acidification promotes keratinocyte cell death and exfoliation (Cao et al., 2012). There remains a need for novel uses and methods for the treatment of skin conditions.

SUMMARY

It has surprisingly been determined that peptides with an amino acid sequence corresponding to the C-terminal of soricidin are TRPV3 agonists. These peptides have at least a portion that has sequence identity to the amino acid sequence EGKLSSNDTEGGLCKEFLHPSKVDLPR ("SOR-C27"; SEQ ID NO: 1) or KEFLHPSKVDLPR ("SOR-C13"; SEQ ID NO: 2). Optionally, the peptides described herein include a contiguous string of amino acids corresponding to the C-terminal of soricidin. It was not previously known that peptides with a sequence that corresponds to fragments of soricidin are capable of activating TRPV3 cation channel activity. This is particularly surprising given that peptides with an amino acid sequence corresponding to the C-terminal of soricidin are known to be antagonists of TRPV6. TRPV3 agonists are useful for the treatment of skin disease or skin conditions such as for exfoliating skin, tissue repair or wound healing, for inhibiting hair growth or for the treatment of a condition associated with low levels or activity of TRPV3. TRPV3 agonists are also useful for the treatment of depression or anxiety. It has also surprisingly been determined that fragments of SOR-C13, including a series of fragments from both the N-terminal and C-terminal ends of SOR-C13, are useful for promoting tissue repair in a keratinocyte model of wound healing. In some embodiments, the peptides described herein are useful to promote cell death. In some embodiments, the peptides described herein are useful promote cell death and/or increase the rate of new skin formation.

Accordingly, in one aspect there is provided a method for treating a condition in a subject comprising administering to the subject a Transient Receptor Potential Vanilloid 3 (TRPV3) agonist comprising all or part of a peptide comprising EGKLSSNDTEGGLCKEFLHPSKVDLPR (SEQ ID NO:1). In one embodiment, there is also provided a method of treating a subject to promote tissue repair comprising administering to the subject all or part of a peptide comprising EGKLSSNDTEGGLCKEFLHPSKVDLPR (SEQ ID NO:1). In some embodiments, the methods described herein are useful for treating a subject with a condition that would benefit from tissue repair. In one embodiment, the tissue is skin tissue. In one embodiment the tissue is nerve tissue. In one embodiment, the condition is a skin condition, cosmetic condition or disease. In one embodiment, the condition is acne, psoriasis or dermatitis. In one embodiment, the subject has one or more wounds and the condition is wound healing. In one embodiment, the wound is a cut, abrasion, laceration, fissure, puncture wound, or contusion. In one embodiment, the wound is a surgical wound, thermal wound or chemical wound. In one embodiment, the condition is unwanted hair growth such as hirsutism. In one embodiment, the methods described herein are useful for preventing unwanted hair growth in a particular area. In one embodiment, the methods described herein are useful for removing the presence of dead skin, i.e.

exfoliation. In one embodiment, the methods described herein are useful for increasing the rate of new skin formation. In one embodiment, the methods described herein are useful for reducing the signs of skin aging or improving the look and/or feel of skin tissue in the subject. Optionally, the peptides described herein are topically administered to a subject, such as to a particular or localized area of tissue, such as skin. In one embodiment, the TRPV3 agonist is administered to an area of skin or tissue that is wounded or affected by a condition. In one embodiment the area of skin or tissue that is wounded or affected by a condition comprises keratinocytes. In one embodiment, the peptides described herein promote the migration and/or proliferation of keratinocytes. In one embodiment, the condition is depression or anxiety.

Also provided is the use of all or part of a peptide comprising EGKLSSNDTEGGLCKEFLHPSKVDLPR (SEQ ID NO: 1) for the treatment of a condition in a subject in need thereof, such as a condition that would benefit from tissue repair or a condition associated with low levels or activity of TRPV3. In one embodiment, there is provided the use of all or part of a peptide comprising EGKLSSNDTEGGLCKEFLHPSKVDLPR (SEQ ID NO: 1) to promote tissue repair in a subject in need thereof. In one embodiment, the peptide is a TRPV3 agonist. In one embodiment, the tissue is skin tissue. In one embodiment, the tissue is nerve tissue. In one embodiment, the condition is a skin condition, cosmetic condition or disease. For example, in one embodiment, the condition is acne, psoriasis, dermatitis, wound healing, unwanted hair growth (hirsutism), or the presence of dead skin. In one embodiment, the peptides described herein are useful for treating a wound in a subject or to promote wound healing. In one embodiment, the wound is a cut, abrasion, laceration, fissure, puncture wound, or contusion. In one embodiment, the wound is a surgical wound, thermal wound or chemical wound. In one embodiment, the peptides described herein are useful for removing the presence of dead skin, i.e. exfoliation. In one embodiment, the peptides described herein are useful for increasing the rate of new skin formation. In one embodiment, the peptides described herein are useful for reducing the signs of skin aging or improving the look and/or feel of skin tissue in the subject. Optionally, the peptides are formulated to be topically administered to a subject, such as to a particular or localized area of tissue, such as skin. In one embodiment, the TRPV3 agonist or peptide is administered to, or for use at, an area of skin or tissue that is wounded or affected by a condition. In one embodiment the area of skin or tissue that is wounded or affected by a condition comprises keratinocytes. In one embodiment, the TRPV3 agonists or peptides described herein promote the migration and/or proliferation of keratinocytes. In one embodiment, the condition is depression. In one embodiment, the condition is depression or anxiety.

Also provided is a method for activating TRPV3 cation channel activity in a cell comprising contacting the cell with all or part of a peptide comprising EGKLSSNDTEGGLCKEFLHPSKVDLPR (SEQ ID NO:1). In one embodiment, the peptide is a TRPV3 agonist comprising all or part of SEQ ID NO:1 as described herein as described herein. Optionally, the cell is in vitro, in vivo or ex vivo. In one embodiment, the cell is a keratinocyte. In one embodiment, the cell is a neuron. In one embodiment, activating TRPV3 cation channel activity in a cell promotes the migration and/or proliferation of the cell. In some embodiments, activating TRPV3 cation channel activity in the cell causes death of the cell. In some embodiments, activating TRPV3 cation channel activity in skin tissue causes the death of skin cells and/or increases the rate of new skin formation.

In one aspect, the peptides described herein comprise between 5 and 27 contiguous amino acid residues of the amino acid sequence EGKLSSNDTEGGLCKEFLHPSKVDLPR (SEQ ID NO:1). For example, in one embodiment, the peptide is a TRPV3 agonist that comprises at least 5, 6, 7, 8, 9, 10 or greater than 10 contiguous amino acids of SEQ ID NO: 1. In one embodiment, the peptide comprises at least 11, 12, 13, 14, 15 or greater than 15 contiguous amino acids of SEQ ID NO: 1 or the C-terminus of SEQ ID NO: 1. Optionally, the TRPV3 agonist has at least 70%, at least 75%, at least 80%, at least 85%, at least 90%, or at least 95% identity to the amino acid sequence KEFLHPSKVDLPR ("SOR-C13" (SEQ ID NO: 2); amino acids nos. 15 to 27 of SEQ ID NO: 1) or to the amino acid sequence EGKLSSNDTEGGLCKEFLHPSKVDLPR (SEQ ID NO: 1). In one embodiment, the TRPV3 agonist comprises, consists essentially of, or consists of the amino acid sequence KEFLHPSKVDLPR, or EGKLSSNDTEGGLCKEFLHPSKVDLPR (SEQ ID NO: 1). In one embodiment, the TRPV3 agonist is a homolog, analog, mimetic, fragment or derivative of all or part of the amino acid sequence EGKLSSNDTEGGLCKEFLHPSKVDLPR (SEQ ID NO: 1) or KEFLHPSKVDLPR.

In one embodiment, the peptide comprises an amino acid sequence with at least 80%, at least 85, at least 90%, or at least 95% sequence identity to an amino acid sequence selected from EGKLSSNDTEGGLCKEFLHPSKVDLPR (SEQ ID NO:1), KEFLHPSKVDLPR (SEQ ID NO: 2), FLHPSKVDLPR (SEQ ID NO: 3), HPSKVDLPR (SEQ ID NO: 4), SKVDLPR (SEQ ID NO: 5), KVDLPR (SEQ ID NO: 6), VDLPR (SEQ ID NO: 7), FLHPSKVDL (SEQ ID NO: 8), FLHPSKV (SEQ ID NO: 9) and FLHPS (SEQ ID NO: 10). In one embodiment, the peptide comprises, consists essentially of, or consists of a peptide selected from EGKLSSNDTEGGLCKEFLHPSKVDLPR (SEQ ID NO:1), KEFLHPSKVDLPR (SEQ ID NO: 2), FLHPSKVDLPR (SEQ ID NO: 3), HPSKVDLPR (SEQ ID NO: 4), SKVDLPR (SEQ ID NO: 5), KVDLPR (SEQ ID NO: 6), VDLPR (SEQ ID NO: 7), FLHPSKVDL (SEQ ID NO: 8), FLHPSKV (SEQ ID NO: 9) and FLHPS (SEQ ID NO: 10).

In one embodiment, the peptide comprises, consists essentially of, or consists of between 5 and 11 contiguous amino acids of KEFLHPSKVDLPR (SEQ ID NO: 2). In one embodiment, the peptide consists of 30 or fewer, 27 or fewer, 25 or fewer, 20 or fewer, 15 or fewer, 13 or fewer, 11 or fewer, 9 or fewer, or 7 or fewer amino acids. In one embodiment, the peptide does not have paralytic activity. In one embodiment, the peptide consists of between 5 and 9 contiguous amino acids of HPSKVDLPR (SEQ ID NO: 4). In one embodiment, the peptides described herein are formulated for topical use, such as in a pharmaceutically or cosmetically acceptable formulation or composition.

In one embodiment, there is also provided a composition comprising a TRPV3 agonist such as a peptide as described herein in combination with a pharmaceutically or cosmetically acceptable carrier. For example, in one embodiment there is provided a composition comprising a peptide as described herein along with an emollient, and optionally an active agent such as an alpha-hydroxy acid.

Also provided is a peptide as described herein for use in the treatment of a condition in a subject in need thereof, such as a condition that would benefit from tissue repair or a condition associated with low levels or activity of TRPV3. In one embodiment, there is provided a peptide for use in promoting tissue repair. In one embodiment, there is provided a peptide for use in promoting wound healing or for the treatment of wounds. In one embodiment, the peptide is a TRPV3 agonist. In one embodiment, the peptide comprises, consists essentially of, or consists between 5 and 27 contiguous amino acid residues of the amino acid sequence EGKLSSNDTEGGLCKEFLHPSKVDLPR (SEQ ID NO:1). In one embodiment, the peptide consists of between 5 and 9 contiguous amino acids of HPSKVDLPR (SEQ ID NO: 4).

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from the detailed description.

BRIEF DESCRIPTION OF THE DRAWINGS

Embodiments of the invention will now be described in relation to the drawings in which.

DESCRIPTION OF VARIOUS EMBODIMENTS

The present description provides new methods for activating TRPV3 and associated methods and uses of peptides that comprise all or part of the C-terminal amino acid sequence of soricidin. Peptides that comprise all or part of the C-terminal amino acid sequence of soricidin have surprisingly been shown to be TRPV3 agonists.

Figure 1:
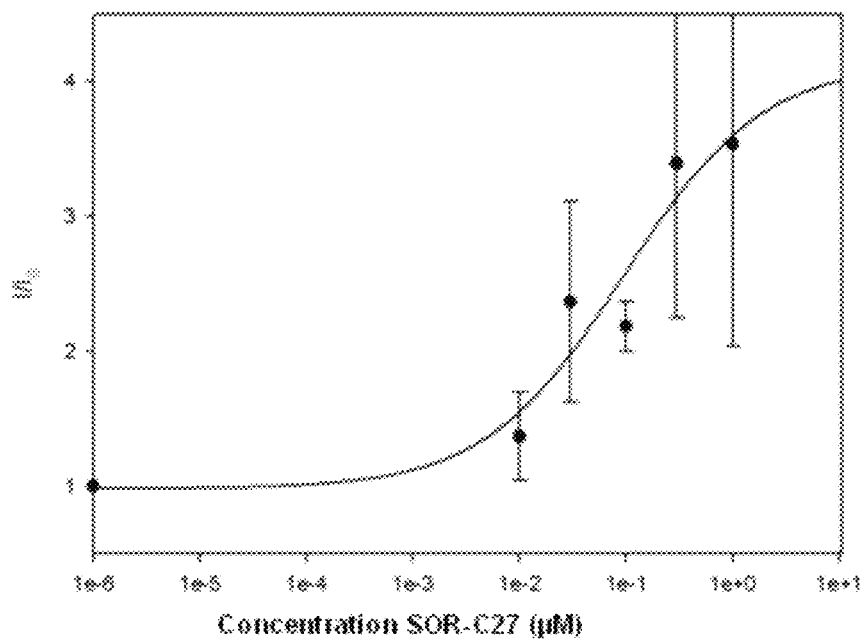
FIG. 1 shows the agonistic dose response of SOR-C27 in TRPV3 channels expressed in HEK-293 cells (EC50=0.0941 µM R=0.9601). The data are mean±SEM (n=6).
Figure 2:
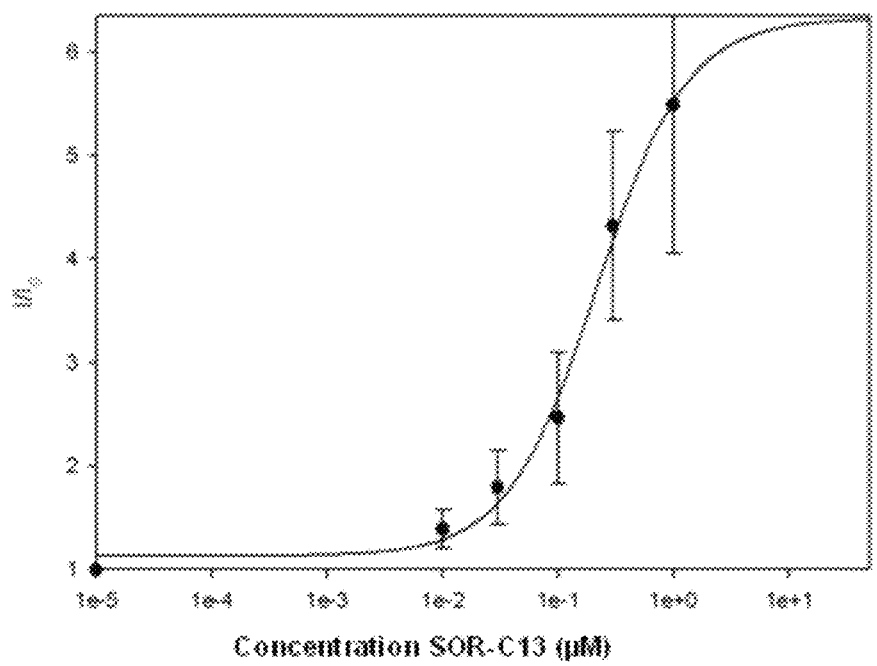
FIG. 2 shows the agonistic dose response of SOR-C13 on TRPV3 channels expressed in HEK-293 cells. The data are mean±SEM n=6 (EC50=0.02169 µM, R=0.09965).

As shown in Example 1 and FIG. 1, SOR-C27 is an effective agonist of TRPV3 and exhibited a half maximal effective concentration ($EC_{50}$) of 0.0941 µM. Furthermore, as shown in FIG. 2 SOR-C13 also activates TRPV3 and exhibited an EC50 of 0.02169 µM. The activation of TRPV3 is known to be involved in a number of physiological processes, such as, but not limited to, exfoliation, would healing and inhibiting hair growth. TRPV3 agonists are also known to cause anxiolytic-like and antidepressive-like behavioral effects in wild-type (WT) mice.

Furthermore, as shown in Example 2, Western blots of cell lysates of an immortalized human keratinocyte cell line (HaCaT) with TRPV3 antibodies, demonstrated that TRPV3 is expressed at much higher levels than TRPV6 in keratinocytes. A series of peptides comprising all or part of SOR-C27 were then tested for their effect on cell death and tissue repair in a wound healing assay using HaCaT cells. As shown in Examples 3-5, many of these peptides were effective at promoting cell death and/or tissue repair. Given the known effect of TRPV3 agonists on collagen production, the peptides described herein which are useful for promoting cell death and tissue repair are expected to be useful for the treatment of a variety of skin diseases and/or conditions including increasing the rate of new skin formation, reducing the signs of aging such as wrinkles or sagging skin and improving the look and/or feel of skin tissue.

In some embodiments, the peptides described herein are therefore useful for the treatment of disorders associated with TRPV3 signaling. In some embodiments, the peptides described herein are useful for promoting tissue repair. In some embodiments, the peptides described herein are useful for treating skin conditions, such as for treating a wound or a skin disease in a subject in need thereof. In one embodiment, the peptides comprise, consist essentially of, or consist of between 5 and 27 contiguous amino acids of SOR-C27 (SEQ ID NO: 1). Also provided are peptides comprising all or part of the N or C-terminal portions of SOR-C13. In some embodiments, the peptides promote the migration and/or proliferation of keratinocytes. In some embodiments, the peptides promote cell death in keratinocytes. In some embodiments, the peptides promote the migration and/or proliferation of keratinocytes at lower concentrations and promote cell death at higher concentrations. In one embodiment, the peptides comprise, consist essentially of, or consist of between 5 and 11 contiguous amino acids of SEQ ID NO: 2. In one embodiment, the peptide consists of between 5 and 9 contiguous amino acids of HPSKVDLPR (SEQ ID NO: 4).

In one aspect of the disclosure the TRPV3 agonists and associated methods described herein are useful for the treatment, cure prevention or suppression of symptoms associated with a disease, disorder, cosmetic condition or medical condition. In one embodiment, there is provided a method for treating a condition in a subject comprising administering to the subject a TRPV3 agonist comprising all or part of a peptide comprising EGKLSSNDTEGGLCK-EFLHPSKVDLPR (SOR-C27; SEQ ID NO:1). Also provided are uses of the TRPV3 agonists described herein for the treatment, cure prevention or suppression of symptoms associated with a disease, disorder, cosmetic condition or medical condition. In one embodiment, the peptides described herein are useful for the treatment of a condition associated with low levels or activity of TRPV3 in a subject.

In one embodiment, the methods described herein are useful for the treatment of a cosmetic condition or skin condition. Cao et al. (2012) reported that TRPV3 channel in keratinocytes is potently activated by intracellular acidification induced by the alpha-hydroxyl acid (AHA) glycolic acid and noted that TRPV3 and noted that TRPV3-mediated proton-sensing and cell death in keratinocytes may serve as a molecular basis for the cosmetic use of AHAs and their therapeutic potential in skin disorders. Accordingly, the TRPV3 agonists described herein are useful for treatment of skin conditions and disorders. In one embodiment the TRPV3 agonists described herein are useful for exfoliating skin, reducing the signs of aging and improving the overall look and/or feel of skin. Furthermore, as demonstrated in Examples 3 and 5, in some embodiments the peptides described herein promote cell death in keratinocytes, which may promote or increase the rate of formation of new skin. Optionally, in one embodiment, the TRPV3 agonists described herein may be used in combination with AHA or other compounds known in the art of chemical peels for the treatment of skin or skin conditions.

In one embodiment, the methods and uses described herein are useful for the treatment of wounds and/or wound healing. Miyamoto et al. (2012) examined nitric oxide (NO) production in the skin where NO plays important roles in wound-healing. Activation of TRPV3 was shown to induce NO production via a nitrite-dependent pathway and TRPV3 and nitrite are involved in keratinocyte migration in vitro and in wound-healing and thermosensory behaviors in vivo. Accordingly, the TRPV3 agonists described herein are useful for treatment of wounds and wound healing in a subject in need thereof.

As set out in Examples 4 and 5, in some embodiments the peptides described herein are useful for promoting tissue repair in a subject in need thereof. As used herein "tissue repair" refers to the process by which damage to the cellular make-up, architecture, connectivity and/or extracellular matrix of a tissue is modified to improve the function or appearance of a tissue or organ. In one example, tissue repair include the process of wound healing. In one example, tissue repair includes the increasing the rate of formation of new skin. In one embodiment, tissue repair includes promoting the migration and/or proliferation of cells that make up the tissue.

As used herein, "wound" refers to any damage to the cellular make-up, architecture, connectivity and/or extracellular matrix of a tissue or combination of tissues. In one embodiment, "wound" is a skin wound that damages the dermis of the skin. In one example, the wound is a cut, abrasion, laceration, fissure, puncture wound, or contusion. Optionally, the wound results in damage to veins and/or arteries and results in internal or external bleeding. In one example, the wound is a surgical wound, such as an intentional or unintentional wound inflicted to a subject during surgery. In one example, the wound is a chemical wound, such as a wound caused by an acid, base, oxidizing agent or other chemical substance that causes tissue damage. In one example, the wound is a thermal wound, such as a burn or frostbite wherein deviations from normal body temperature in the subject causes tissue damage.

In one embodiment, the methods and uses described herein are useful for increasing the production of collagen in skin. Lee et al. (2008) showed that the use of carvacrol, an agonist of TRPV3, increases cellular calcium concentrations and collagen production in dermal fibroblasts. Accordingly, the TRPV3 agonists described herein are useful for boosting production of collagen in a subject in need thereof.

In one embodiment, the methods and uses described herein are useful for inhibiting hair growth. Borbiro et al. (2011) investigated the role of TRPV3 in the regulation of human hair growth using human organ-culture hair follicles and cultures of human outer root sheath (ORS) keratinocytes. TRPV3 activation resulted in a dose-dependent inhibition of hair shaft elongation, suppression of proliferation, and induction of apoptosis and premature hair follicle regression. Accordingly, the TRPV3 agonists described herein are useful for inhibiting hair growth and for the treatment of conditions marked by unwanted hair growth such as hirsutism.

In one embodiment, the methods described herein are useful for the treatment of an anxiety or depression. Moussaieff et al. (2008) investigated the role of TRPV3 channels in the brain and noted that incensole acetate (IA), a Boswellia resin constituent, is a potent TRPV3 agonist that causes anxiolytic-like and antidepressive-like behavioral effects in wild-type (WT) mice with concomitant changes in c-Fos activation in the brain. Moussaieff et al. also noted that the behavioral effects were not observed in TRPV3(−/−) mice, suggesting that they are mediated via TRPV3 channels. Accordingly, the TRPV3 agonists described herein are useful for the treatment of anxiety and/or depression.

In one embodiment, the TRPV3 agonist comprises from 5 to 27 contiguous amino acids of SEQ ID NO: 1. In one embodiment, the TRPV3 agonist comprises contiguous amino acids of SEQ ID NO: 1 starting from the N-terminal amino acid of SEQ ID NO: 1. In another embodiment, the TRPV3 agonist comprises contiguous amino acids starting from the C-terminal sequence of SEQ ID NO: 1. In one embodiment, the TRPV3 agonist comprises at least 5, 6, 7, 8, 9, 10 or greater than 10 contiguous amino acids of SEQ ID NO:1. Optionally the TRPV3 agonist comprises at least: 10, 11, 12, 13, 14, 15, 16, 17, 18, 19 or 20 amino acids of SEQ ID NO: 1. In one embodiment, the TRPV3 agonists described herein comprise, consist essentially of, or consist of the amino acid sequence KEFLHPSKVDLPR (SORC-13) or EGKLSSNDTEGGLCKEFLHPSKVDLPR (SOR-C27).

In some embodiments, amino acids may be added to the TRPV3 agonists described herein. One can readily make longer peptides by adding a variety of additional amino acids to the SOR-C27 sequence to make a TRPV3 agonist peptide that could be up to, for example, 30, 35, 40 or 45 amino acids long (e.g. additional amino acids corresponding to the soricidin amino acid sequence such as one or more of the amino acids that are immediately towards the N-terminal segment of SOR-C27 in soricidin (SILARPAELNTETCI-LEC; SEQ ID NO: 2), a targeting sequence, or other amino acids) or longer. In one embodiment, the peptide consists of 30 or fewer, 27 or fewer, 25 or fewer, 20 or fewer, 15 or fewer, 13 or fewer, 11 or fewer, 9 or fewer, or 7 or fewer amino acids.

In some embodiments, TRPV3 agonists and peptides described herein that activate the TRPV3 cation channel activity are readily identified with assays known in the art suitable for measuring TRPV3 cation channel activity. For example, in one embodiment, a peptide having TRPV3 cation channel activation activity is identified by determining that the peptide increases calcium channel activity by modulating (i.e., increasing) the flow of calcium through TRPV3. TRPV3 cation channel activation activity can readily be measured using a cell line transfected with an expression vector for TRPV3 and a patch-clamp assay as set out in Example 1. Peptides suitable for the methods and uses described herein can also be identified using a wound healing assay using keratinocytes, such as described in Example 3.

The TRPV3 agonists described herein optionally include analogs of the aforementioned peptides. Analogs of the peptides of the invention optionally include, but are not limited to an amino acid sequence containing one or more amino acid substitutions, insertions, deletions and/or mutations. Amino acid substitutions may be of a conserved or non-conserved nature. Conserved amino acid substitutions involve replacing one or more amino acids of the peptides of the invention with amino acids of similar charge, size, and/or hydrophobicity characteristics. When only conserved substitutions are made, the resulting analog should be functionally equivalent. Non-conserved substitutions involve replacing one or more amino acids of the amino acid sequence with one or more amino acids that possess dissimilar charge, size, and/or hydrophobicity characteristics. The analog is optionally a peptoid, which is an N-substituted polyglycine with amino acid R groups attached at the N atom. Another analog is optionally a peptide synthesized from D-amino acids rather than the natural L-amino acids.

One or more amino acid insertions are optionally introduced into the TRPV3 agonists described herein such as SOR-C13 or SOR-C27 or any one of SEQ ID NOS: 1 to 10. Amino acid insertions consist of single amino acid residues or sequential amino acids ranging for example from 2 to 15 amino acids in length.

Deletions consist of the removal of one or more amino acids, or discrete portions from the amino acid sequence of the peptide. The deleted amino acids may or may not be contiguous.

Analogs of a peptide or TRPV3 agonist of the invention are optionally prepared by introducing mutations in a nucleotide sequence encoding the peptide. Mutations in nucleotide sequences constructed for expression of analogs of a protein of the invention preserve the reading frame of the coding sequences. Furthermore, the mutations will preferably not create complementary regions that could hybridize to produce secondary mRNA structures such as loops or hairpins, which could adversely affect translation of the mRNA.

Mutations are optionally introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures are employed to provide an altered gene having particular codons altered according to the substitution, deletion, or insertion required. Deletion or truncation of a peptide of the invention is also readily achieved by utilizing convenient restriction endonuclease sites adjacent to the desired deletion. Subsequent to restriction, overhangs may be filled in, and the DNA re-ligated. Exemplary methods of making the alterations set forth above are disclosed by Sambrook et al. (Sambrook J et al. 2000. Molecular Cloning: A Laboratory Manual (Third Edition), Cold Spring Harbor Laboratory Press).

In addition, peptides, TRPV3 agonists and/or analogs useful for the purposes of the present invention are readily prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart). The TRPV3 agonists of the invention also include peptides having sequence identity to a peptide of the invention, mutated peptides and/or truncations thereof as described herein.

Other peptides and TRPV3 agonists suitable for the methods and uses of the present invention optionally comprise, consist essentially of or consist of an amino acid sequence with at least: 30%, 40%, 50%, 60%, 70%, 75%, 80%, 85%, 90% or 95% sequence identity to all or part of SEQ ID NO:1 described herein that activate TRPV3 cation channel activity. In one embodiment, the peptide or TRPV3 agonist has at least 70%, at least 75%, at least 80%, at least 85%, at least 90% or at least 95% sequence identity to the amino acid sequence KEFLHPSKVDLPR (SOR-C13) or EGKLSSNDTEGGLCKEFLHPSKVDLPR (SOR-C27). In one embodiment, the peptide or TRPV3 agonist has at least 70%, at least 75%, at least 80%, at least 85%, at least 90% or at least 95% sequence identity to any one of SEQ ID NOS: 1 to 10. Sequence identity is typically assessed by the BLAST version 2.1 program-advanced search (parameters as above; Altschul, S. F., Gish, W., Miller, W., Myers, E. W. & Lipman, D. J. (1990) "Basic local alignment search tool." J. Mol. Biol. 215:403-410). BLAST is a series of programs that are available online through the U.S. National Center for Biotechnology Information (National Library of Medicine Building 38A Bethesda, Md. 20894) The advanced Blast search is set to default parameters. References for the Blast Programs include: Altschul, S. F., Gish, W., Miller, W., Myers, E. W. & Lipman, D. J. (1990) "Basic local alignment search tool." J. Mol. Biol. 215:403-410; Gish, W. & States, D. J. (1993) "Identification of protein coding regions by database similarity search." Nature Genet. 3:266-272; Madden, T. L., Tatusov, R. L. & Zhang, J. (1996) "Applications of network BLAST server" Meth. Enzymol. 266:131-141; Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402); Zhang, J. & Madden, T. L. (1997) "PowerBLAST: A new network BLAST application for interactive or automated sequence analysis and annotation." Genome Res. 7:649-656).

In one embodiment, the peptides or TRPV3 agonists suitable for the methods and uses of the present invention are peptide mimetics. In one embodiment, the peptide mimetics are based on all or part of EGKLSSNDTEGGLCK-EFLHPSKVDLPR (SEQ ID NO: 1) or KEFLHPSKVDLPR and increase TRPV3 channel activity. "Peptide mimetics" are structures which serve as substitutes for peptides in interactions between molecules (See Morgan et al (1989), Ann. Reports Med. Chem. 24:243-252 for a review). Peptide mimetics include synthetic structures which optionally contain amino acids and/or peptide bonds but retain the structural and functional features of a peptide, or enhancer or inhibitor of the invention. Peptide mimetics also include peptoids, oligopeptoids (Simon et al (1972) Proc. Natl. Aced, Sci USA 89:9367); and peptide libraries containing peptides of a designed length representing all possible sequences of amino acids corresponding to a peptide of the invention.

Peptide mimetics are designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

In one embodiment, the TRPV3 agonists described herein are administered to a subject. For example, in one embodiment, the TRPV3 agonists are administered to a subject to treat a skin condition or disorder. In one embodiment, the TRPV3 agonists are administered to a subject for the inhibition of hair growth, or the treatment of hirsutism, or to increase the rate of new skin formation. In one embodiment, the TRPV3 agonists are administered to a subject to promote tissue repair, for the treatment of wounds or for wound healing. In one embodiment, the TRPV3 agonists are administered to a subject for the treatment of anxiety or depression.

The term "subject" as used herein includes all members of the animal kingdom and is preferably mammalian, such as human. Administering a TRPV3 agonist to a subject includes both in vivo and ex vivo administrations. In a preferred embodiment, the TRPV3 agonist is topically applied to the skin of a subject. Optionally, The TRPV3 agonist is applied along with one or more cosmetically acceptable carriers such as emollients or stabilizers.

As used herein, and as well understood in the art, "treating" or "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease or disorder, preventing spread of disease or disorder, delay or slowing of disease or disorder progression, amelioration or palliation of the disease or disorder state, and remission (whether partial or total), whether detectable or undetectable. "Treatment" can also mean prolonging survival as compared to expected survival if not receiving treatment. Optionally, the term "treatment" includes cosmetic treatments of the skin to improve the overall look and/or feel of the skin or to reduce the signs of aging.

In one embodiment the TRPV3 agonists described herein can be formulated into a cosmetic or pharmaceutical composition for administration to subjects in a biologically compatible form. The term "biologically compatible form suitable for administration in vivo" refers to a form of the substance to be administered in which any toxic effects are outweighed by the therapeutic effects. The TRPV3 agonists may be administered to living organisms including humans, and animals. In a preferred embodiment, the TRPV3 agonists are formulated for topical administration to the skin.

Administration of a therapeutically active amount of the TRPV3 agonists or pharmaceutical compositions of the present invention is defined as an amount effective, at dosages and for periods of time necessary to achieve the desired result, such as exfoliation or would healing. For example, a therapeutically active amount of a substance may vary according to factors such as the condition, age, sex, and weight of the individual, and the ability of the substance to elicit a desired response in the individual. Dosage regimes may be adjusted to provide the optimum therapeutic or cosmetic response. For example, several divided doses may be administered daily or the dose may be proportionally reduced as indicated by the exigencies of the therapeutic or cosmetic situation. In one embodiment, compositions comprising the TRPV3 agonists described herein are topically applied to a subject.

The TRPV3 agonists of the invention are preferably combined with other components such as a carrier in a composition such as a pharmaceutical composition or cosmetic composition. The compositions are useful when administered in methods of cosmetic treatment or treatment or prevention of a condition associated with TRPV3 pathophysiology. Optionally, the TRPV3 agonists described herein are combined with other known substances useful for the treatment of skin conditions. In one embodiment, the TRPV3 agonists described herein are combined with other known anti-anxiety or anti-depressive agents.

The TRPV3 agonists described herein or compositions comprising the TRPV3 agonists can be administered to humans or animals by a variety of methods including, but not restricted to topical administration, oral administration, aerosol administration, intratracheal instillation, intraperitoneal injection, injection into the cerebrospinal fluid, intravenous injection and subcutaneous injection. Dosages to be administered depend on patient needs, on the desired effect and on the chosen route of administration. For example, the pharmaceutical compositions can be on a bandage, which is used for wound healing. Nucleic acid molecules encoding for the TRPV3 agonists described herein and the TRPV3 agonist polypeptides may be introduced into cells using in vivo delivery vehicles such as liposomes. They may also be introduced into these cells using physical techniques such as microinjection and electroporation or chemical methods such as coprecipitation or using liposomes.

The compositions are prepared by known methods for the preparation of pharmaceutically or cosmetically acceptable compositions which can be administered to subjects, and such that an effective quantity of the TRPV3 agonist is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA) or Handbook of Pharmaceutical Additives (compiled by Michael and Irene Ash, Gower Publishing Limited, Aldershot, England (1995). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. Optionally, the compositions described herein include one or more emollients, fragrances and/or stabilizers. In one embodiment, the compositions described herein are useful for exfoliating keratinocytes and include a TRPV3 agonist and one or more alpha-hydroxyl acids such as glycolic acid.

On this basis, the pharmaceutical compositions optionally includes an active compound or substance, such as a TRPV3 agonist peptide as described herein or nucleic acid molecule encoding such a TRPV3 activator, in association with one or more pharmaceutically acceptable vehicles or diluents, and contained in buffered solutions with a suitable pH and iso-osmotic with the physiological fluids. Methods of combining the active molecules with the vehicles or combining them with diluents are well known to those skilled in the art. The composition optionally includes a targeting agent for the transport of the active compound to specified sites within tissue.

The following examples illustrate embodiments of the invention and do not limit the scope of the invention.

Example 1: Patch-Clamp Testing of TRPV3 with SOR-C13, SOR-C27 and SOR-N54

SOR-C13, SOR-C27 and SOR-N54 were tested using a patch clamp screen to determine whether the peptide had any effect on the channel activity of TRPV3. Ruthenium red, a known antagonist of TRPV3 and 2-Aminoethoxydiphenyl Borate (2-APB) a known activator of TRPV3 were used as controls. As set out below, SOR-C13 and SOR-C27 were determined to be agonists of TRPV3 channel activity with an EC50 of 0.02169 µM and 0.0941 µM respectively. The peptide SOR-N54 did not show any effect on TRPV3 channel activity.

Materials & Methods:
Cell Culture and Expression of TRPV3 cDNA

HEK 293 cells were maintained in 030 mm cell culture plate in DMEM media supplemented with 10% fetal bovine serum and penicillin/streptomycin. Cells were grown in a humidified atmosphere of 95% air/5% $CO_2$ at 37° C. in a cell culture incubator.

The cells from 70-90% confluence were prepared for transfection. For transient expression in HEK-293 cells 1 µg plasmid cDNA and pEGFP (in vivo reporter of gene expression) were used.

A. Electrophysiological Recording Methods

Recordings were performed at 20-23° C. Currents were sampled using Digidata 1440A, amplified, and filtered at 2 kHz using Axopatch 200B, then acquired and analyzed using pClamp 10.0 (Molecular Devices, Sunny vales, CA, USA).

The pipette solution and bath solution contained 140 mM CsCl, 4 mM $MgCl_2$, 10 mM EGTA, CsOH pH=7.3 and 130 mM NaCl, 5 mM KCl, 2 mM $CaCl_2$, 1 mM $MgCl_2$, 25 mM HEPES, 30 mM Glucose, pH=7.3, respectively.

B. Test Peptide Application, Data Acquisition and Curve Fitting Methods

Each peptide was diluted in the bath solution to the desired concentration (0.01 µM, 0.03 µM, 0.1 µM, 0.3 µM, 1 µM, 3 µM, or 10 µM), respectively.

Results

Figure 3A:
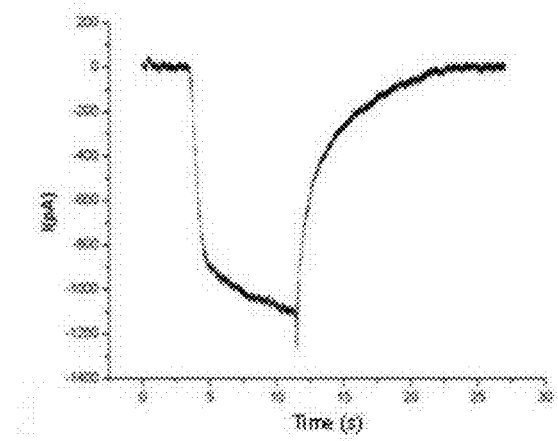
FIG. 3A and FIG. 3B show the activation of TRPV3 channel with 100 µM 2-APB in the absence (FIG. 3A) and presence (FIG. 3B) of 10 µM SOR-N-54.
Figure 3B:
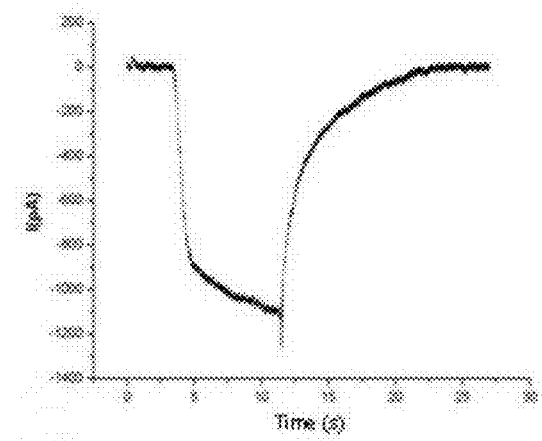
Figure 4A:
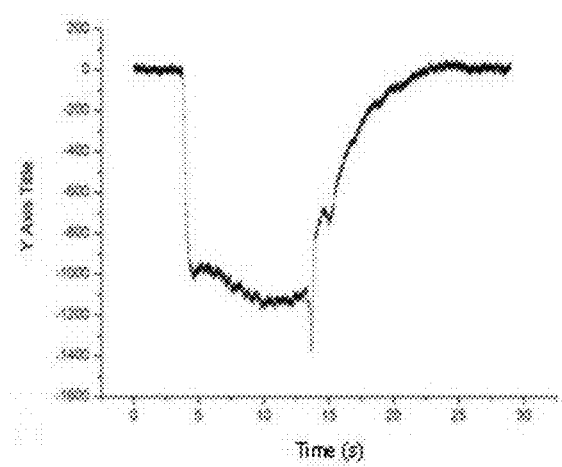
FIG. 4A and FIG. 4B show the activation of TRPV3 channel with 100 µM 2-APB in the absence (FIG. 4A) and presence (FIG. 4B) of the control inhibitor Ruthenium Red.
Figure 4B:
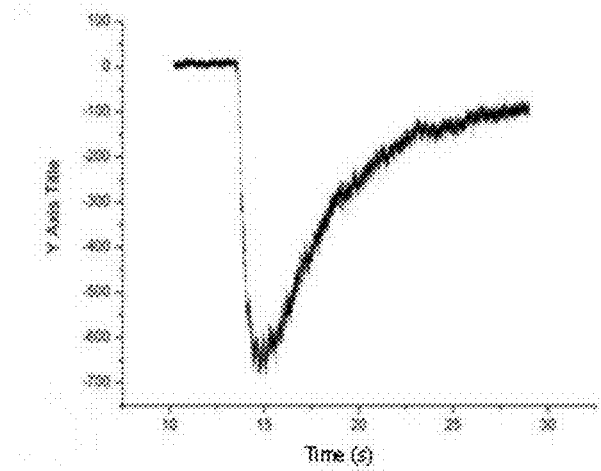

As shown in FIG. 1, SOR-C27 exhibited an agonistic dose-response in TRPV3 patch clamp studies with an EC50 of 0.0941 µM. SOR-C13 also displayed an agonistic dose-response in TRPV patch clamp studies with an EC50 of 0.02169 µM. In contrast, 10 µM SOR-N54 (full length soricidin peptide) did not alter the activation of TRPV3 in the presence of 100 µM 2-APB, while the presence of Ruthenium red inhibited activation of the channel by 2-APB (FIGS. 3, and 4).

Example 2: Expression of TRPV3 in Human Keratinocytes

Figure 5A:
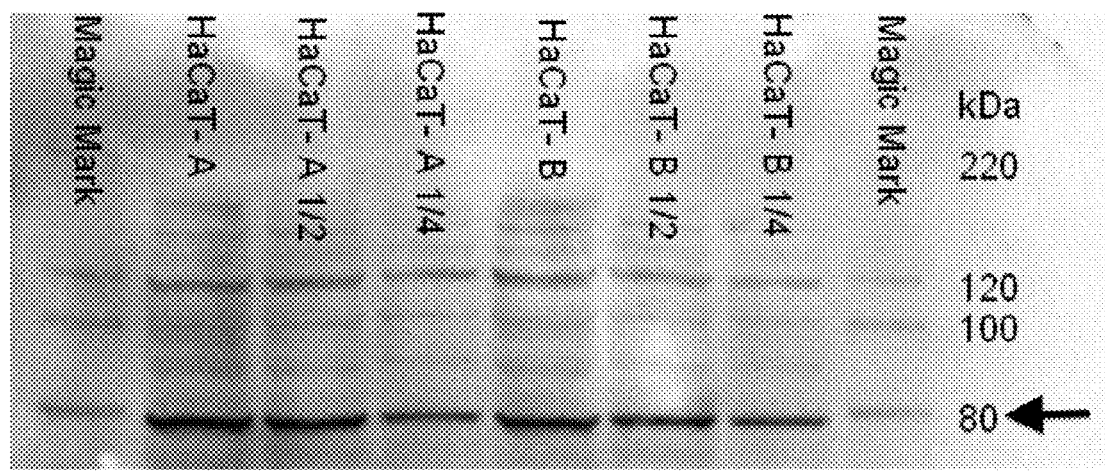
FIG. 5A shows and SDS-PAGE gel and Western Blot of lysates of two batches of the human keratinocyte cell line (HaCaT). The lysates were successively diluted (½, ¼) and probed with human anti-TRPV3. The arrow indicates the TRPV3 protein band about 80 kDa.
Figure 5B:
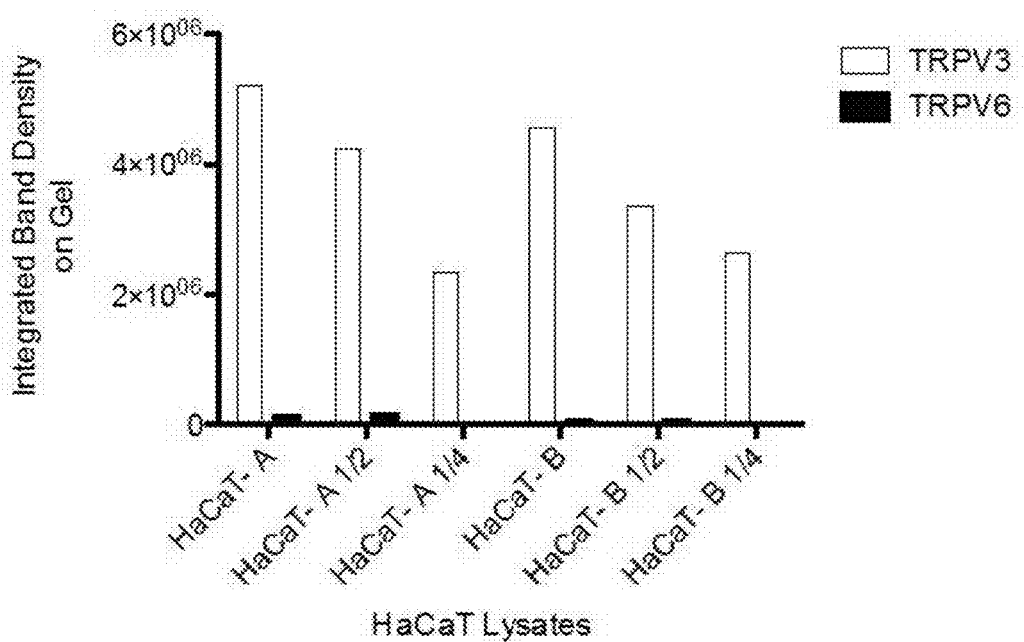
FIG. 5B shows Western Blot band densities measured from the gel in FIG. 5A.

An immortalized human keratinocyte cell line (HaCaT) was tested for the expression of TRPV3. Lysates of HaCaT cells were tested by Western Blotting for the presence of TRPV3 using TRPV3-specific antibodies. As shown in FIG. 5A, the resulting gel shows bands indicative of TRPV3 (indicated by the arrow) at about 80 kDa. The band density for these bands with different dilutions of the lysate is shown plotted in FIG. 5B. Another known target of SOR-C13, TRPV6, is present in only small traces in this cell line, providing evidence that the major target of these peptides in keratinocytes is likely TRPV3.

Example 3: Effect of SOR-C13 and SOR-C27 on Cell Death

Figure 6:
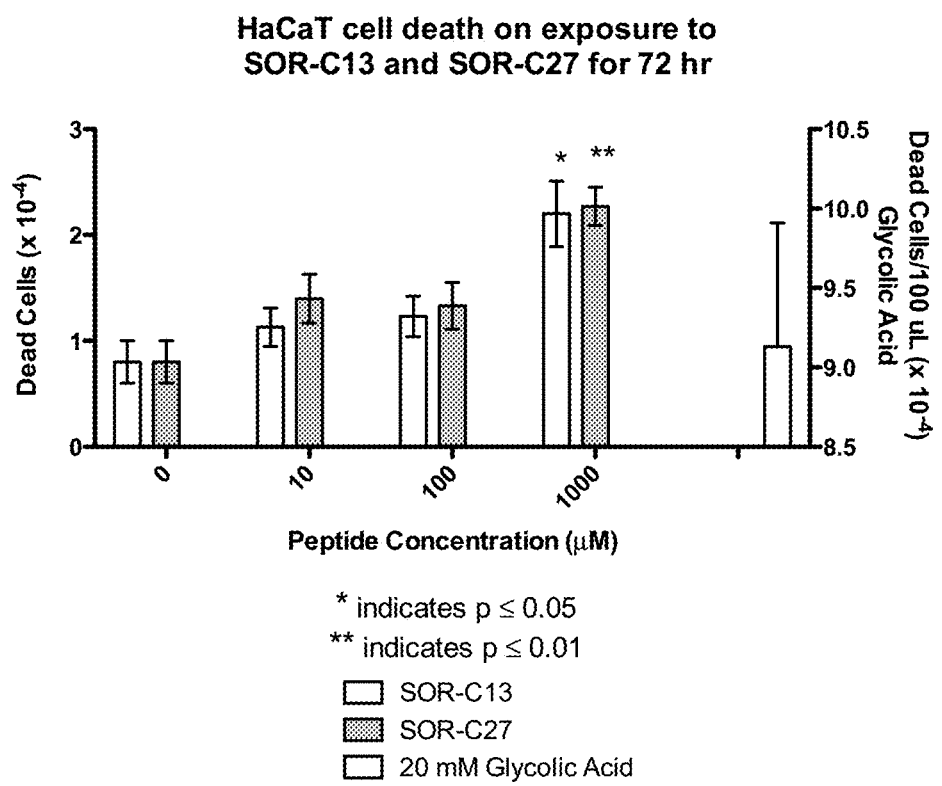
FIG. 6 shows the number of counted dead cells in HaCaT cultures after exposure to treatments with different concentrations of SOR-C13 and SOR-C27 for 72 hours compared to a no-treatment control and 20 mM Glycolic Acid (an alpha-hydroxy acid).

In an initial experiment, various concentrations of SOR-C13 and SOR-C27 were tested on human keratinocytes (HaCaT cells) for their ability to cause cell death. The negative control was Phosphate Buffered Saline (PBS) and the positive control was Glycolic Acid (20 mM), a known activator of TRPV3. At the concentrations used (10, 100 and 1000 uM) only the 1000 uM concentration produced a statistically significant increase in cell death over PBS (FIG. 6). It is likely that equimolar concentrations of peptides and glycolic acid would have shown the peptides to be more effective. The two peptides appeared to be indistinguishable in their activity with respect to the number of dead cells Materials and Methods
Formulation Both peptides were dissolved in PBS at 30 mM concentration at ambient temperature based on the peptide content with a correction factor (SOR-C13 concentration was multiplied by 1.19, while SOR-C27 concentration was multiplied by 1.29). Stock solutions were sterilized by passing through a 0.2 µm syringe filter prewashed with PBS. Stocks of peptides were kept at −20° C. during the study.

Cell Culture

Human immortalized keratinocyte HaCaT cells (Cat. # T0020001) were from Addexbio Technologies (San Diego, Calif., USA). In general, HaCaT cells were cultured in 37° C. $CO_2$ incubator in DEME with 1.0 g/L glucose (Lonza, Cat #12-707F) with 10% FBS. Glutamine (2 mM), penicillin (100 I.U.) and streptomycin (100 µg/ml) were added to the media. Cells were sub-cultured twice per week using Trypsin-0.25% EDTA to detach cells.

Cell Death Assay

HaCaT cells were plated at ~$8\times10^5$/well in each well of the 12-well tissue culture plates in triplicates in 2 ml culture media. Twenty-four (24) hours post-plating, cells were treated with PBS, or SOR-C13 at 10, 100 and 1000 µM, or SOR-C27 at 10, 100 and 1000 µM, or glycolic acid at 20 mM.

At 72 hours post-treatment, the incubation was terminated and supernatant was collected. Attached cells were washed with 2 ml PBS, and trypsinized. Suspension of cells was combined with supernatant and spun at 1000 g for 5 minutes. The cell pellet was then resuspended in 100 µl PBS for cell counting using trypan blue exclusion.

Student's t-test was used to compare the group treated with a test article vs. the group treated with PBS. Standard errors of mean (SEM) were used to represent variation of data.

Results

After the 72-hour treatment, the cell numbers (live) in PBS-treated wells were around $3.6 \times 10^5$ per well. Numbers of dead cells in PBS-treated wells were $\sim 8 \times 10^3$ per well. As shown in FIG. 6, no significant difference in the numbers of dead cells was found in wells treated with PBS compared to those treated with SOR-C13 or SOR-C27 up to 100 μM. However, SOR-C13 or SOR-C27 at 1 mM significantly induced cell death of HaCaT cells compared to PBS treatment (p<0.05). The number of dead cells in wells treated with SOR-C13 or SOR-C27 (both at 1 mM) was $\sim 2.2 \times 10^4$/well or $2.3 \times 10^4$/well, respectively. Glycolic acid (20 mM) dramatically induced cell death of HaCaT cells under the experimental condition. Number of dead cells in wells treated with glycolic acid (20 mM) reached $\sim 9.1 \times 10^4$ per well.

Both SOR-C13 and SOR-27 at the highest concentration tested (1 mM) induced approximately a 2 fold increase in cell death compared to PBS treatment in HaCaT cells after a 72-hour incubation period. SOR-C13 or SOR-C27 at lower concentrations (10 or 100 μM) did not have a significant effect on induction of cell death in HaCaT cells.

Example 4: Effect of SOR-C13 and SOR-C27 on Tissue Repair

SOR-C13 and SOR-C27 were tested for their ability to promote tissue repair in a human keratinocytes (HaCaT) model of wound healing. In this model, cells are grown to confluency and then a gap is made in the sheet of cells by scratching the surface of the cells. After treating the cells for 24 hours, the closure of the gap, and the state of the cells in terms of polarization and mobility into the gap, are measured as a surrogate for activation of the wound healing response and the proliferation and/or migration of cells involved in tissue repair.

In the present example, SOR-C13 appeared to promote tissue repair in a dose responsive manner while SOR-C27 did not appear to exert a significant effect.

Wound Healing Assay

HaCaT cells were plated at $4 \times 10^5$ per well in 12-well tissue culture plates in MEGM Bullet Kit (Lonza, Cat. # CC-3150) containing bovine pituitary extracts (BPE), hEGF, insulin, and hydrocortisone. The total volume was 2 ml. About 24 hours later, a gap at the bottom of each well was generated by scratching with a sterile pipette tip. The supernatant was aspirated and cells were washed gently once with PBS. Fresh media (MEGM Bullet Kit, 2 ml) was added after the wash. Cells were treated in duplicates with PBS, or SOR-C13 at 10, 100 and 1000 μM, or SOR-C27 at 10, 100 and 1000 μM, and 100 μM valproic acid. After 24 hours, each well was examined under the microscope to semi-quantify the gap closure by cell migration. A digital camera fixed to the microscope was used to capture images of cells.

Under visual inspection, the wound healing results was scored as:
- "−": minimal cell polarization toward wound, no initiation of cell protrusion into the gap; no change in the wound gap;
- "+": cell polarization toward wound was observed; cell protrusion was observed; cell migration started but gap size is between 75 to 100% of original wound gap;
- "++": cell polarization toward the wound was observed; cell protrusion was observed; cell migration across the gap was observed, and gap size ½ of original wound gap;
- "+++": cell polarization toward wound was observed; cell protrusion was observed; cell migration across the gap was observed, and gap size ⅓ of original wound gap.

Results

Figure 7:
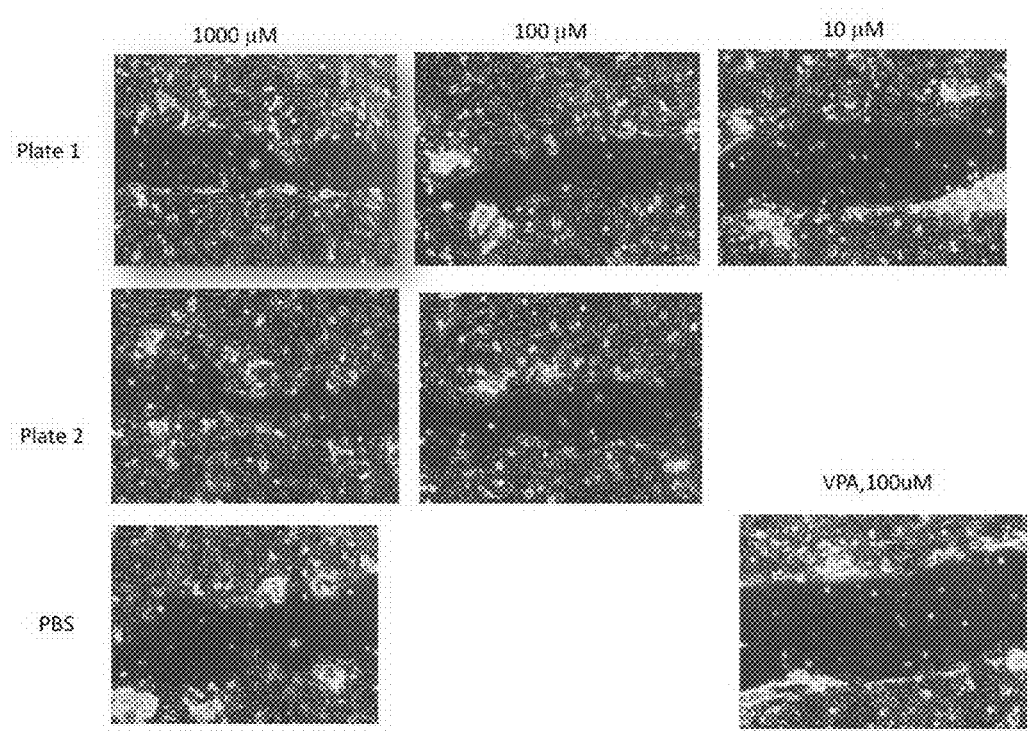
FIG. 7 shows the migration of HaCat cells in a wound healing assay following treatment with SOR-C13 as described in Example 4.

As shown in FIG. 7, HaCaT cells treated with PBS (lower left panel) started to migrate and/or proliferate through the gap created by a scratch after 24 hours. Remarkably, SOR-C13 exhibited a dose-dependent effect on promoting the migration of HaCaT cells through the scratch (Table 1). At 10 μM (top right panel), SOR-C13 had little difference compared to PBS treatment on cell migration. At 100 μM (top center panel), SOR-C13 clearly had an effect to induce cell migration (wound healing) of HaCaT cells. The gap of cells was dramatically closed by SOR-C13 at 1000 μM compared to treatment at lower doses (10-100 μM) of SOR-C13.

TABLE 1

Semi-quantitative assessment of the gap closure activity of SOR-C13 in a HaCaT wound model system.

| SOR-C13 Treatment | Migration Score |
| --- | --- |
| PBS | + |
| 10 uM | + |
| 100 uM | ++ |
| 1000 uM | +++ |

Figure 8:
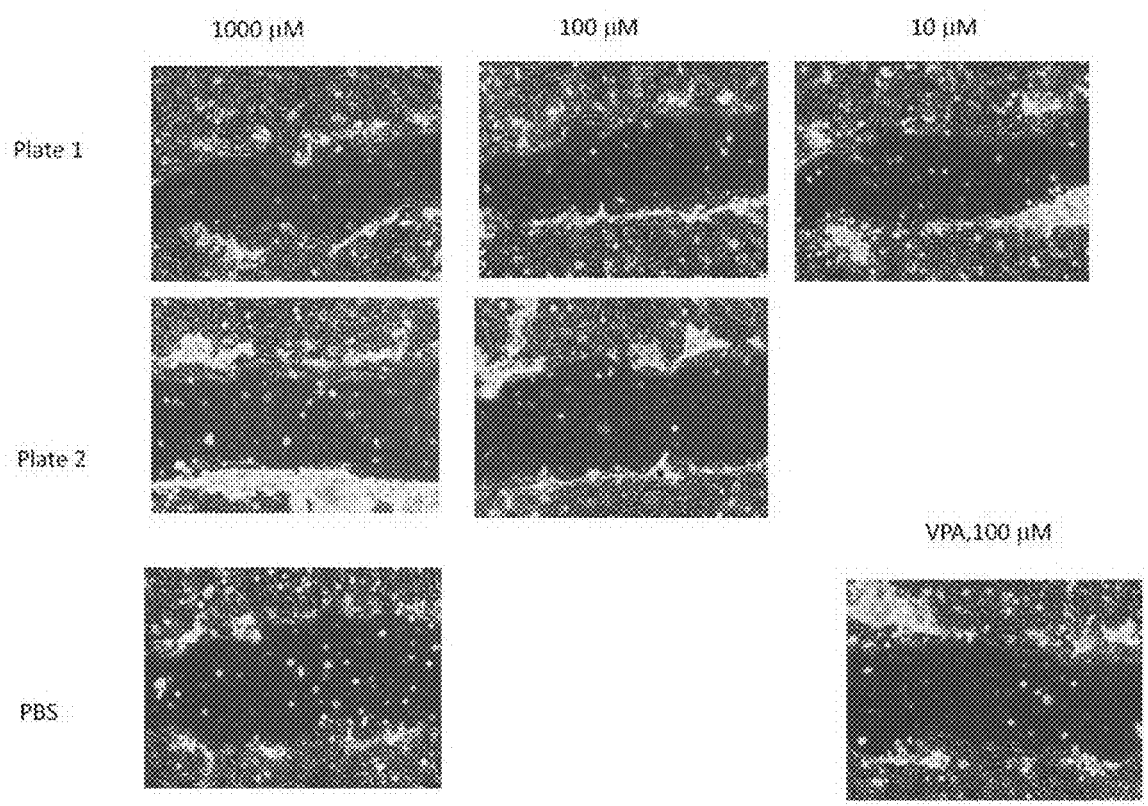
FIG. 8 shows the migration of HaCat cells in a wound healing assay following treatment with SOR-C27 as described in Example 4.

In contrast, SOR-C27 did not appear to have a clear effect on the migration of HaCaT cells (FIG. 8) under the present test conditions and the gap in cells treated by SOR-C27 at 10, 100, 1000 μM had no significant visual difference compared to that treated by PBS. Valproic acid at 100 μM appeared to block the migration of HaCaT cells under the present test conditions.

Discussion

SOR-C13 induced migration of HaCaT cells in a dose-dependent manner. At concentrations equal or higher than 100 μM, SOR-C13 promoted wound healing of HaCaT cells upon 24-hour incubation. In contrast, SOR-C27 up to 1 mM had no clear effect on promoting migration of HaCaT cells under the present test conditions, however valproic acid at 100 μM also did not appear to induce migration of HaCaT cells. Based on the present test results, it is expected that further testing of SOR-C27 under different test conditions may result in migration and/or proliferation of the keratinocytes.

Example 5: Effect of SOR-C13 Fragments on Cell Death and Tissue Repair

A series of peptides were synthesized that were successive 2-amino acid truncations of SOR-C13. These peptide fragments were then tested for their ability to induce cell death and promote tissue repair in human keratinocytes using a wound healing assay.

SOR-C13 and the series of 8 peptide fragments (SOR-C11, SOR-C9, SOR-C7, SOR-C6, SOR-05, SOR-CN9, SOR-CN7, and SOR-CN5) that were tested are listed in Table 2. All peptides were synthesized by CanPeptide Inc. (265 Blvd Hymus, Suite 1500, Pointe-Claire, Quebec H9R 1G6). SOR-C27 (MW 2957, batch number P091125-08218-3) was synthesized with a reported purity ~77.7% by BACHEM (3132 Kashiwa Street, Torrance, Calif. 90505, USA) with a peptide content of 83.7%. Powdered stocks were received at ambient temperature and stored at −20° C. freezer until use.

TABLE 2

Identification of SOR-C13 Peptide Fragments, SEQ ID NOs and Weight.

| Peptide | Sequence | SEQ ID NO: | Molecular Weight (MW) | Formula Molecular Weight (MW + Salt + Hydrate) |
|---|---|---|---|---|
| SOR-C13 | KEFLHPSKVDLPR | 2 | 1565.9 | 1870.8 |
| SOR-C11 | FLHPSKVDLPR | 3 | 1308.6 | 1563.4 |
| SOR-C9 | HPSKVDLPR | 4 | 1048.2 | 1252.3 |
| SOR-C7 | SKVDLPR | 5 | 814 | 972.5 |
| SOR-C6 | KVDLPR | 6 | 726.9 | 868.5 |
| SOR-C5 | VDLPR | 7 | 598.7 | 715.3 |
| SOR-CN9 | FLHPSKVDLPR | 8 | 1055.2 | 1260.7 |
| SOR-CN7 | FLHPSKV | 9 | 827 | 988.1 |
| SOR-CN5 | FLHPS | 10 | 599.7 | 716.5 |

Formulation

Solutions of each of the peptides listed in Table 2 were made based on formulation weight without correction of purity in PBS at a 100 mM stock concentration. Stock solutions were sterilized by passing through a 0.2 μm syringe filter prewashed with PBS. Stocks of peptides were kept in aliquots at −20° C. during the study. Glycolic acid was made in a 5M stock in PBS and filtered using a 0.2 μm syringe filter and kept at −20° C.

Cell Culture

Human immortalized keratinocyte HaCaT cells were cultured as described in Example 3.

Cell Death Assay

HaCaT cells were plated at ~8×10$^5$/well in each well of the 12-well tissue culture plates in triplicates in 2 ml culture media. Twenty-four (24) hours post-plating, cells were treated with PBS, or peptide stocks at 100 and 1000 μM (in triplicates), or glycolic acid at 20 mM (single data point). The Cell Death Assay was otherwise performed as described in Example 3.

Wound Healing Assay

HaCaT cells were plated at 1.6×10$^5$ per well in 24-well tissue culture plates in 1 ml of DMEM low glucose medium with 10% FBS. After 3 days, when the cells in each well were ~100% confluent, a gap at the bottom of each well was generated by scratching with a sterile pipette tip. Supernatant was aspirated and cells were washed gently once with PBS. Fresh media (MEGM Bullet Kit, (Lonza, Cat. # CC-3150) containing bovine pituitary extracts (BPE), hEGF, insulin, and hydrocortisone was added after the wash with peptides. After 24 hours, cells were fixed with 2% paraformaldehyde with 15-minute incubation. Fixed cells were rinsed with PBS. Cells in each well were then examined under the microscope to semi-quantify the gap closure by cell migration. A digital camera fixed to the microscope was used to capture images of cells. The width of gap was measured by a ruler semi-quantitatively on the image. Under visual inspection, the wound healing results were also scored as "−"; "+"; "++"; or "+++" using the same criteria as set out in Example 4.

Results

Cell Death

After a 72-hour treatment, the cell numbers of both live and dead cells were recorded. The number of dead cells in PBS-treated HaCaT cells was ~3.8×10$^4$ per well, which accounted for 4-8% of total cells recorded. In contrast, the number of dead cells in glycolic acid treated cells was only slightly higher ~4.5×10$^4$. Under the conditions of the present assay, glycolic acid appeared to have more of an effect with respect to growth inhibition than for induction of cell death.

Figure 9:
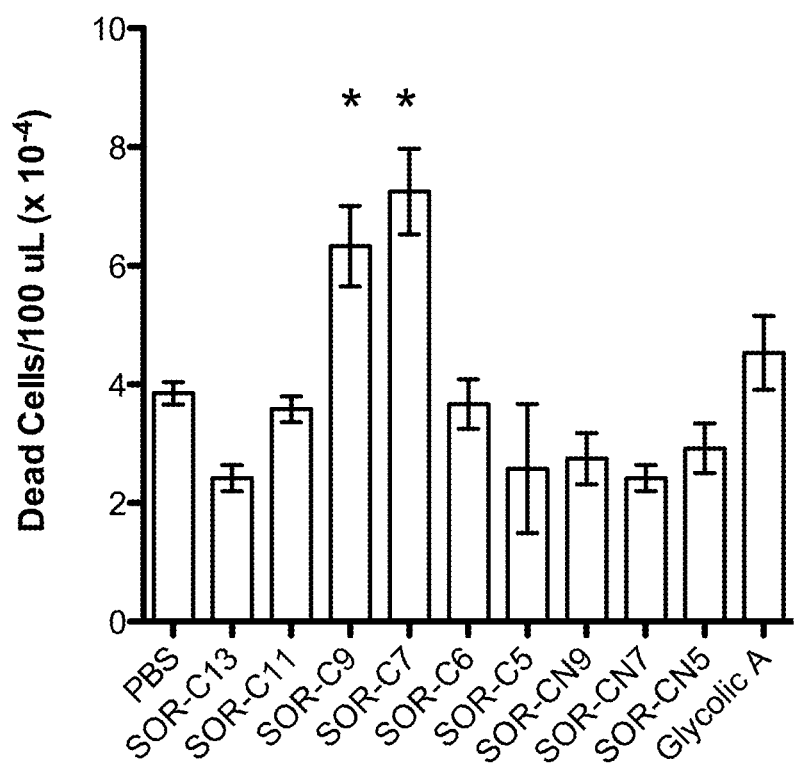
FIG. 9 shows the number of counted dead cells after treatment with a library of peptide fragments derived from SOR-C13. The values are the mean±SEM, n=2 with p<0.05 indicated by asterisks

The number of dead cells following treatment with the peptides of Table 2 is shown in FIG. 9. Treatment of HaCaT cells with SOR-C7 (both at 100 and 1000 μM) and SOR-C9 (at 100 μM) led to a slight but significant increase of cell death (*, $p<0.05$). All other peptides, including SOR-C13, had no significant effect to induce cell death of HaCaT cells under the conditions of the present assay.

As shown in FIG. 9, it appears that the initiation of cell death is more effective using peptides derived from the C-terminal end of SOR-C13. The responses to SOR-C13 and glycolic acid were unlike the results set out in Example 3 in that there was no increase in cell death above the PBS treatment. It is likely that the advanced passage number of this series of cell cultures could have influenced the response (10-15 passages instead of 3-5 passages in earlier experiments). Furthermore, the two assays differed in the plating density of cells in each series of experiments (8×10$^5$/well versus 3×10$^5$/well). Nevertheless, there was significant cell death induction for the C9 and C7 derivatives at 100 uM.

Wound Healing

The effect of the peptides on tissue repair was determined using a wound healing assay that measures the migration of HaCaT cells. Gap size prior to and after treatment was semi-quantified by measuring the size of each gap on a digital photograph of the cells.

Figure 10:
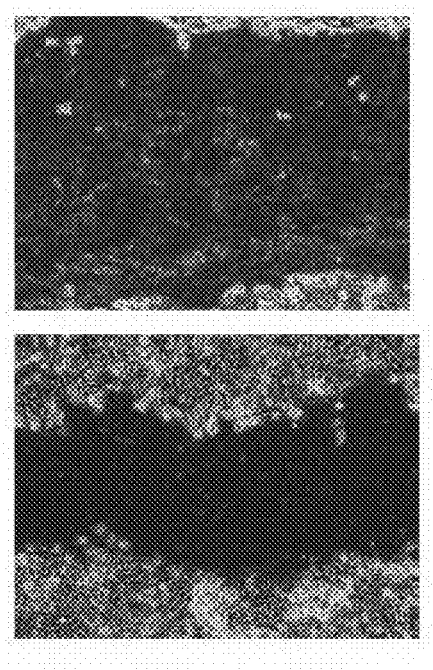
FIG. 10 shows the migration of HaCaT cells in the wound assay treated with PBC at Time 0 (top panel) and after 24 hours (lower panel) post scratch.

HaCaT cells (treated with PBS) started to migrate through the gap within 24 hours. At 24 hours post scratch, the gap size was ~61% compared to the original gap size at time 0 (100%), as shown in FIG. 10.

Figure 11:
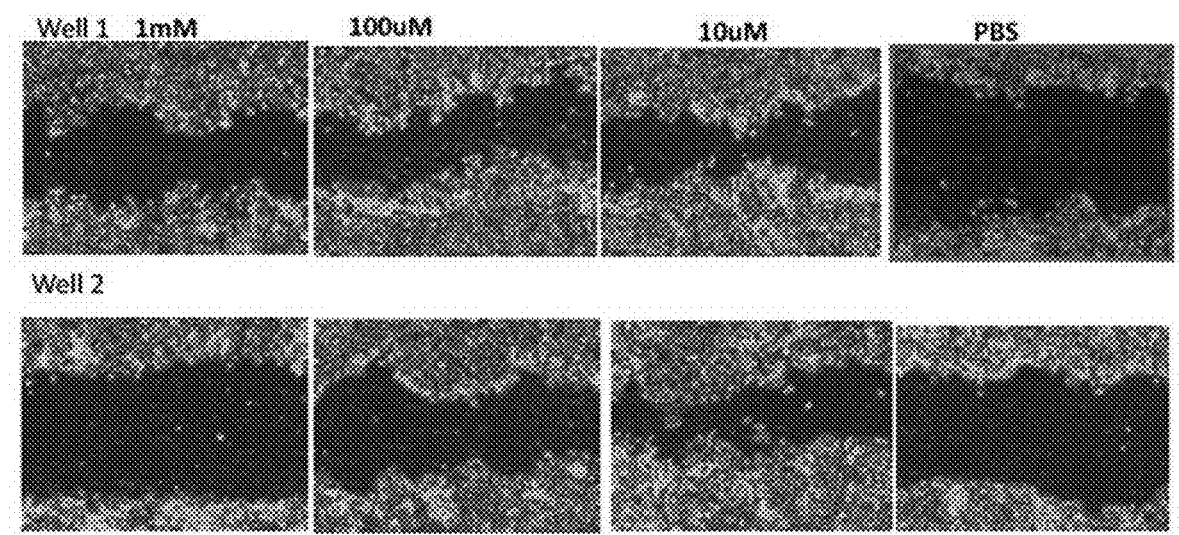
FIG. 11 shows the gap closure observed in the wound healing assay with different concentrations of SOR-C13 in two test runs as set out in Example 5. It appears that the lower concentrations are more effect than higher concentrations at promoting tissue repair and the migration and/or proliferation of cells.

The gap closure effect of the mobilized HaCaT cells treated with SOR-C13 compared to PBS in two different test runs is shown in FIG. 11. It appears that lower concentrations of SOR-C13 are more effective than higher concentrations to promote tissue repair and wound healing.

Figure 12:
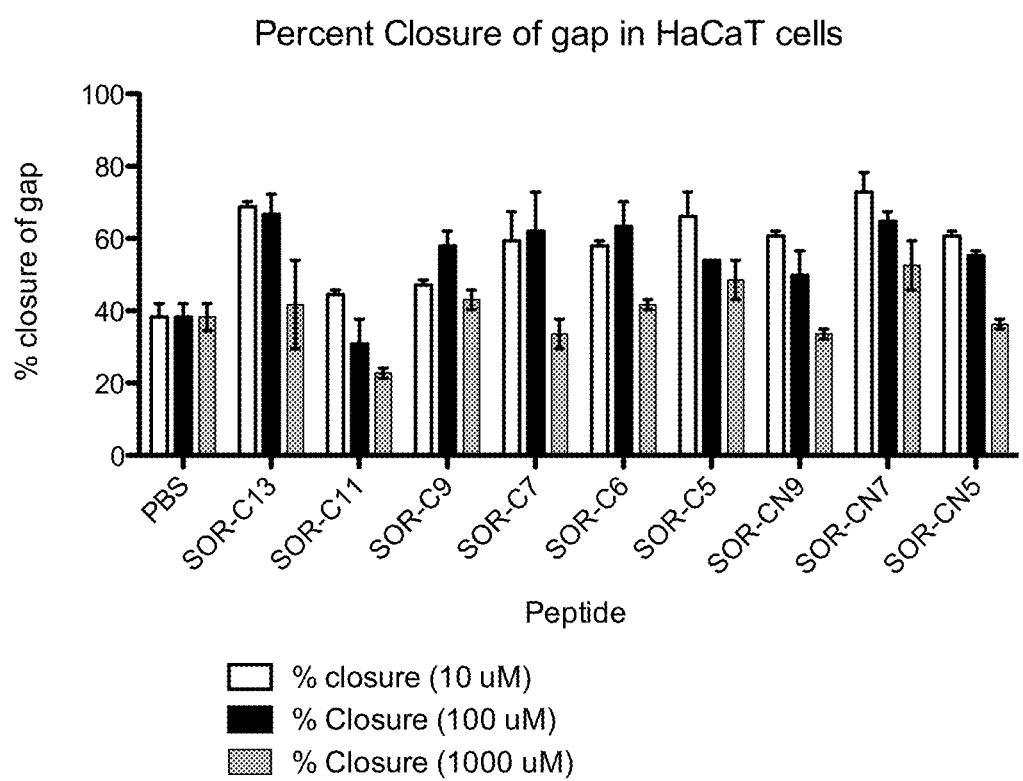
FIG. 12 shows the degree of gap closure in the wound healing assay as a function of treating the HaCaT cells with different concentrations of the peptides listed in Table 2. The values are mean+/−SEM, n=2

FIG. 12 shows the results of the wound healing assay for the series of peptides as the percent of gap closure at each of the three different concentrations (10, 100 and 1000 μM). In each case, the wound healing response was greater at the lowest concentration. One explanation is that at the higher concentrations of peptide, the cell death program is initiated instead. In this experiment, SOR-C13 elicited very good response at the two lowest concentrations, with no response at 1000 uM.

Comparison of Induction of Cell Death and Wound Healing Activity

Figure 13:
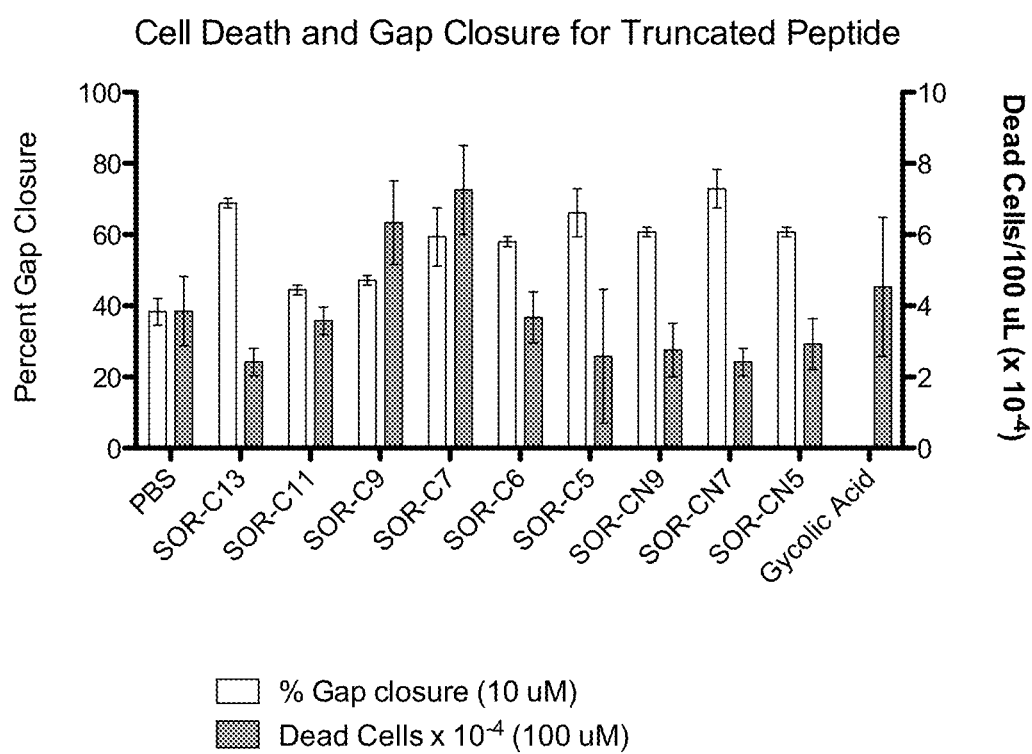
FIG. 13 shows a comparison of the cell death response and would healing response for the peptides listed in Table 2. The cell death response and the wound healing response appear to be maximal at different ends of SOR-C13 and at about a 10-fold difference in concentration.

The sensitivity of the HaCaT cells to the peptides for the wound-healing phenomenon appears to be far greater than for the induction of cell death (10 uM compared to 100 uM). Additionally, as shown in FIG. 13, the activity with respect to cell death induction appears to be associated more with the C-terminal end of SOR-C13 and the N-terminal sections appear to be more active in inducing the wound healing response.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Borbíró I, Lisztes E, Tóth B I, Czifra G, Oláh A, Szöllosi A G, Szentandrássy N, Nánási P P, Péter Z, Paus R, Kovacs L and Biró T. Activation of transient receptor potential vanilloid-3 inhibits human hair growth. *J Invest Dermatol.* 2011 August; 131(8):1605-14.

Cao X, Yang F, Zheng J and Wang K. Intracellular Proton-mediated Activation of TRPV3 Channels Accounts for the Exfoliation Effect of α-Hydroxyl Acids on Keratinocytes. *J Biol Chem.* 2012 Jul. 27; 287(31):25905-16.

Lee J, Jung E, Yu H, Kim Y, Ha J, Kim Y S, and Park D. Mechanisms of carvacrol-induced expression of type I collagen gene. J Dermatol Sci. 2008 December 52(3): 160-169.

Miyamoto T, Petrus M J, Dubin A E, and Patapoutian A. TRPV3 regulates nitric oxide synthase-independent nitric oxide synthesis in the skin. *Nat Commun.* 2011 Jun. 28; 2:369.

Moussaieff A, Rimmerman N, Bregman T, Straiker A, Felder C C, Shoham S, Kashman Y, Huang S M, Lee H, Shohami E, Mackie K, Caterina M J, Walker J M, Fride E and Mechoulam R. Incensole acetate, an incense component, elicits psychoactivity by activating TRPV3 channels in the brain. FASEB J. 2008 August; 22(8):3024-34.

The invention claimed is:

1. A method of promoting skin repair in a subject in need thereof comprising administering a topical formulation comprising a peptide consisting of 7, 8, or 9 contiguous amino acids of SEQ ID NO: 4 and an emollient to the skin of the subject in an amount that promotes the migration and/or proliferation of keratinocytes in the skin.

2. The method of claim 1 wherein the formulation is administered to a cut, abrasion, or laceration in the subject's skin.

3. The method of claim 1 wherein the peptide consists of SEQ ID NO: 4.

4. The method of claim 1 wherein the peptide consists of SEQ ID NO: 5.

5. The method of claim 1 wherein the formulation further comprises an alpha-hydroxy acid.

6. The method of claim 5 wherein the alpha-hydroxy acid is glycolic acid.

* * * * *

SEQUENCE LISTING

<160> NUMBER OF SEQ ID NOS: 10

<210> SEQ ID NO 1
<211> LENGTH: 27
<212> TYPE: PRT
<213> ORGANISM: Artificial Sequence
<220> FEATURE:
<223> OTHER INFORMATION: Synthetic peptides

<400> SEQUENCE: 1

Glu Gly Lys Leu Ser Ser Asn Asp Thr Glu Gly Gly Leu Cys Lys Glu
1               5                   10                  15

Phe Leu His Pro Ser Lys Val Asp Leu Pro Arg
            20                  25

<210> SEQ ID NO 2
<211> LENGTH: 13
<212> TYPE: PRT
<213> ORGANISM: Artificial Sequence
<220> FEATURE:
<223> OTHER INFORMATION: Synthetic peptides

<400> SEQUENCE: 2

Lys Glu Phe Leu His Pro Ser Lys Val Asp Leu Pro Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic peptides

<400> SEQUENCE: 3

Phe Leu His Pro Ser Lys Val Asp Leu Pro Arg
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic peptides

<400> SEQUENCE: 4

His Pro Ser Lys Val Asp Leu Pro Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptides

<400> SEQUENCE: 5

Ser Lys Val Asp Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptides

<400> SEQUENCE: 6

Lys Val Asp Leu Pro Arg
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptides

<400> SEQUENCE: 7

Val Asp Leu Pro Arg
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptides

<400> SEQUENCE: 8

Phe Leu His Pro Ser Lys Val Asp Leu
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptides

<400> SEQUENCE: 9

Phe Leu His Pro Ser Lys Val
1               5

<210> SEQ ID NO 10
<211> LENGTH: 5
<212> TYPE: PRT
<213> ORGANISM: Artificial Sequence

```
<220> FEATURE:
<223> OTHER INFORMATION: Synthetic peptides

<400> SEQUENCE: 10

Phe Leu His Pro Ser
1               5
```